United States Patent
Butters et al.

(10) Patent No.: US 8,979,848 B2
(45) Date of Patent: Mar. 17, 2015

(54) FORCE LIMITING PERSUADER-REDUCER

(75) Inventors: Joshua A. Butters, Chandler, AZ (US); T. Wade Fallin, Hyde Park, UT (US); Carson Esplin, Logan, UT (US); Nathan Pierce, Logan, UT (US); Greta Jo Hays, Logan, UT (US)

(73) Assignee: Stryker Spine (FR)

( * ) Notice: Subject to any disclaimer, the term of this patent is extended or adjusted under 35 U.S.C. 154(b) by 1045 days.

(21) Appl. No.: 11/904,033

(22) Filed: Sep. 25, 2007

(65) Prior Publication Data

US 2008/0221626 A1 Sep. 11, 2008

Related U.S. Application Data

(60) Provisional application No. 60/846,969, filed on Sep. 25, 2006.

(51) Int. Cl.
*A61B 17/70* (2006.01)
*A61B 19/00* (2006.01)

(52) U.S. Cl.
CPC .......... *A61B 17/7086* (2013.01); *A61B 17/7032* (2013.01); *A61B 19/30* (2013.01); *A61B 2019/4857* (2013.01)
USPC ...................................... 606/86 A

(58) Field of Classification Search
USPC ........... 606/86 A, 86 R, 246–279; 403/322.4, 403/325, 327
See application file for complete search history.

(56) References Cited

U.S. PATENT DOCUMENTS

| | | | |
|---|---|---|---|
| 4,927,425 A | 5/1990 | Lozier | |
| D346,217 S | 4/1994 | Sparker et al. | |
| 5,720,751 A | 2/1998 | Jackson | |
| 6,123,707 A | 9/2000 | Wagner | |
| 6,159,179 A | 12/2000 | Simonson | |
| 6,251,111 B1 | 6/2001 | Barker et al. | |
| 6,440,133 B1 | 8/2002 | Beale et al. | |
| 6,589,259 B1 | 7/2003 | Solingen | |
| 6,648,888 B1 | 11/2003 | Shluzas | |

(Continued)

FOREIGN PATENT DOCUMENTS

| | | |
|---|---|---|
| DE | 4238339 | 5/1994 |
| DE | 29917554 U1 | 12/1999 |

(Continued)

OTHER PUBLICATIONS

Charles Hartjen; The Atavi System, Surgical Technique Brochure. Endius, p. 1-17.

(Continued)

*Primary Examiner* — Eduardo C Robert
*Assistant Examiner* — Steven Cotroneo
(74) *Attorney, Agent, or Firm* — Lerner, David, Littenberg, Krumholz & Mentlik, LLP

(57) ABSTRACT

An apparatus and method for advancement of a spinal rod in a spinal implant, wherein the apparatus includes a body and a handle attached to the body. A shaft is slidably attached to the body, the shaft is coupled to the handle and has a first end adapted to engage the spinal rod. At least one retractor blade is attached to the body and the spinal implant. The operation of the handle results in the shaft persuading the spinal rod in the spinal implant. The force exerted by the shaft on the spinal rod is limited to a pre-selected force. The apparatus can also be operated in a non-limiting mode when a reduction retractor blade is used.

27 Claims, 12 Drawing Sheets

(56) References Cited

U.S. PATENT DOCUMENTS

| | | |
|---|---|---|
| 6,660,006 B2 | 12/2003 | Markworth et al. |
| 6,746,449 B2 | 6/2004 | Jones et al. |
| 6,790,209 B2 | 9/2004 | Beale et al. |
| 2001/0027318 A1 | 10/2001 | Oribe et al. |
| 2002/0045904 A1 | 4/2002 | Fuss et al. |
| 2002/0095153 A1 | 7/2002 | Jones et al. |
| 2003/0009168 A1* | 1/2003 | Beale et al. ............ 606/61 |
| 2003/0073998 A1 | 4/2003 | Pagliuca et al. |
| 2003/0199872 A1 | 10/2003 | Markworth et al. |
| 2003/0225408 A1 | 12/2003 | Nichols et al. |
| 2004/0049191 A1 | 3/2004 | Markworth et al. |
| 2004/0064193 A1* | 4/2004 | Evans et al. .......... 623/23.51 |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147936 A1 | 7/2004 | Rosenberg et al. |
| 2004/0147937 A1 | 7/2004 | Dunbar et al. |
| 2004/0172022 A1 | 9/2004 | Landry et al. |
| 2004/0254576 A1 | 12/2004 | Dunbar et al. |
| 2004/0260287 A1 | 12/2004 | Ferree |
| 2004/0267275 A1 | 12/2004 | Cournoyer et al. |
| 2005/0010221 A1 | 1/2005 | Dalton |
| 2005/0021030 A1 | 1/2005 | Pagliuca et al. |
| 2005/0033299 A1 | 2/2005 | Shluzas |
| 2005/0059969 A1 | 3/2005 | McKinley |
| 2005/0070917 A1 | 3/2005 | Justis |
| 2005/0085813 A1 | 4/2005 | Spitler et al. |
| 2005/0090822 A1 | 4/2005 | DiPoto |
| 2005/0090833 A1 | 4/2005 | DiPoto |
| 2005/0119667 A1 | 6/2005 | Leport et al. |
| 2005/0131407 A1 | 6/2005 | Sicvol et al. |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0137593 A1 | 6/2005 | Gray et al. |
| 2005/0137594 A1 | 6/2005 | Doubler et al. |
| 2005/0192570 A1 | 9/2005 | Jackson |

FOREIGN PATENT DOCUMENTS

| | | |
|---|---|---|
| DE | 20020192 U1 | 3/2001 |
| EP | 1006888 | 6/2000 |
| EP | 1374786 | 1/2004 |
| WO | WO9514437 | 6/1995 |
| WO | 0128440 A3 | 11/2001 |
| WO | 3057055 | 7/2003 |
| WO | WO2004021899 | 3/2004 |
| WO | WO2004037074 | 5/2004 |
| WO | WO2005018466 | 3/2005 |
| WO | WO2005023123 | 3/2005 |
| WO | WO2005032358 | 4/2005 |
| WO | WO2006116662 | 11/2006 |

OTHER PUBLICATIONS

Diapason, Surgical Texchnique Catalog, Diapasan Spinal System, Jan. 2002.

Pathfinder; Minimally Invasive Pedicie Fixation System. Spinal Concepts Product Brochure p. 1-4.

Pathfinder; Minimally invasive Spinal Fixation System and Surgical Technique. Spinal Concepts Product Brochure, p. 1-26.

Sofamor Danek; Eclipse CD Horizon Eclipse Implants and Instruments, Information from the Sofamor Danek Web page, p. 1-3.

Sofamor Danek; Sextant CD Horizon Sextant Rod Insertion System, Sofamor Danek Web page.

International Search Report for Application No. PCT/US2007/020653 dated Mar. 13, 2008.

Written Opinion of the International Searching Authority for Application No. PCT/US2007/020653 dated Mar. 31, 2009.

* cited by examiner

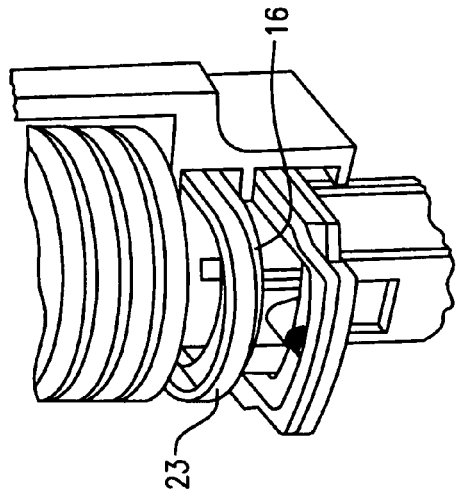
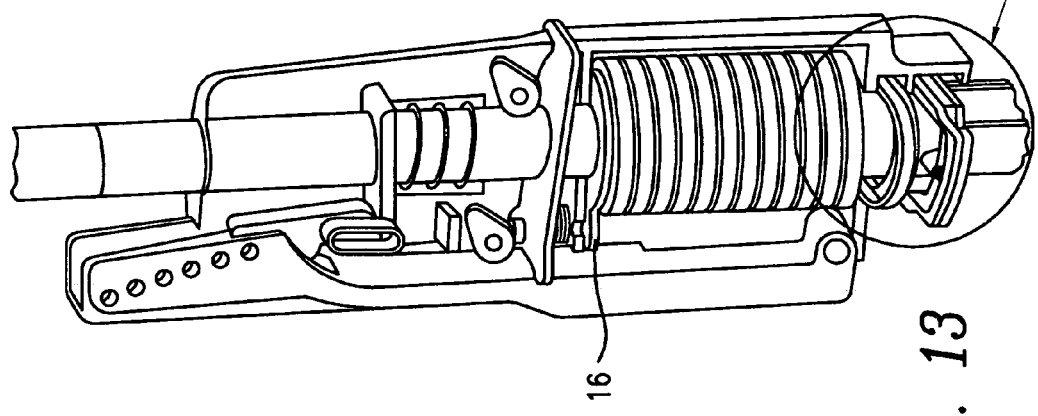
FIG. 14
FIG. 13

FORCE LIMITING PERSUADER-REDUCER

CROSS-REFERENCE TO RELATED APPLICATIONS

The present application claims priority from Provisional Application No. 60/846,969, filed Sep. 25, 2006, the disclosure of which is hereby incorporated herein by reference.

FIELD OF THE INVENTION

The present invention relates to a device and method for urging an orthopedic rod into a recess in an orthopedic device and more particularly, to a device and method for securing a spinal rod to a coupling element.

BACKGROUND OF THE INVENTION

The spinal column is a highly complex system of bones and connective tissues that provides support for the body and protects the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord and nerves is located behind the vertebral bodies.

Disorders, including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

Surgical techniques commonly referred to as spinal fixation use surgical implants and/or mechanical immobilization to fuse two or more vertebral bodies of the spinal column. Spinal fixation may also be used to alter the alignment of adjacent vertebral bodies relative to one another so as to change the overall alignment of the spinal column. Such techniques have been used effectively to treat the above-described conditions and, in many cases, to relieve pain.

One spinal fixation technique involves immobilizing the spine using orthopedic stabilizing rods, commonly referred to as spine rods, which are positioned generally parallel to the spine. This may be accomplished by exposing the spine posteriorly and fastening bone screws to the pedicles of vertebral bodies. The pedicle screws are generally placed two per vertebra and serve as anchor points for the spine rods. Coupling elements or implants adapted for receiving a spine rod therethrough are then used to join the spine rods to the pedicle screws. A set screw or fastener then fastens the spine rod into a seat in a coupling element.

SUMMARY OF THE INVENTION

In one aspect, a device of the present invention includes a force input mechanism and a shaft coupled to the force input mechanism and adapted to move in an axial direction in response to a force being applied to the force input mechanism. A force limiter limits how much of the applied force is transferred from the force input mechanism to the shaft.

In some implementations, the device includes a force limiter lockout mechanism that is adapted to either enable or disable the force limiter. The device is adapted to be coupled to retractor blades of a spinal implant. In some implementations, the lockout mechanism automatically enables or disables the force limiter depending on the type of retractor blade that the device is coupled to.

In another aspect, a method is disclosed that includes transferring an applied force from a force input mechanism of a device to a shaft coupled to an orthopedic rod in a patient and, in response to increase in applied force beyond a predetermined value, limiting the amount of applied force that is transferred from the force input mechanism to the shaft.

According to certain implementations, the method further includes enabling and/or disabling the force limiting function. In some implementations, that enabling/disabling depends on what type of retractor blade(s) the device is coupled to. For example, the force limiting function might be enabled if the device is coupled to a persuasion-type retractor blade. Alternatively, the limiting function might be disabled if the device is coupled to a reduction-type retractor blade.

Various other aspects include: a system for percutaneous advancement of a spinal rod into a spinal implant which has a force-limiting means; a system for percutaneous advancement of a spinal rod into a spinal implant which has both a force-limiting means and a full-force means. In another aspect a system is disclosed for percutaneous advancement of a spinal rod into a spinal implant that includes: a handle adapted to connect to the spinal implant or spinal implant extensions, a force input lever, and a translating shaft. In yet another aspect a system is disclosed for percutaneous advancement of a spinal rod into a spinal implant that includes: a handle, a lever, a translating shaft, and a retractor blade engagement means whereas the spinal implant may be connected to retractor blades and the retractor blades may be connected to the percutaneous advancement system. In another aspect a system is disclosed for percutaneous advancement of a spinal rod into a spinal implant that includes: a handle adapted to connect to the spinal implant or spinal implant extensions, a force input lever, a force input rocker plate, a force retention rocker plate, and a translating shaft.

An object of the invention is to provide an apparatus for advancement of a spinal rod in a spinal implant. The apparatus includes a body and a handle attached to the body. A shaft is slidably attached to the body, the shaft is coupled to the handle and has a first end adapted to engage the spinal rod. At least one retractor blade is attached to the body and the spinal implant. The operation of the handle results in the shaft persuading the spinal rod in the spinal implant. The force exerted by the shaft on the spinal rod is limited to a pre-selected force. The apparatus can also be operated in a non-limiting mode when a reduction retractor blade is used.

Another object of the invention is to provide a method of advancing a spinal rod in a spinal implant. The method includes implanting a first spinal implant in a first vertebra; implanting a second spinal implant in a second vertebra; placing a rod in the first and the second implant; attaching at least one persuasion retractor blade to the first vertebra; attaching a persuading and reducing apparatus to the persuasion retractor blade; and operating the handle on the persuading and reducing apparatus to advance a shaft and thereby persuade the rod in the first spinal implant, the shaft applying a force on the rod that is less than a pre-selected force.

Other features and advantages will be apparent from the following description and drawings.

BRIEF DESCRIPTION OF THE DRAWINGS

FIG. 13 is a cutaway view of a portion of a persuader-reducer device.

FIG. 14 is a detail view of a portion of the cutaway view of FIG. 13.

Like reference numerals refer to like elements.

DETAILED DESCRIPTION

Figure 1:
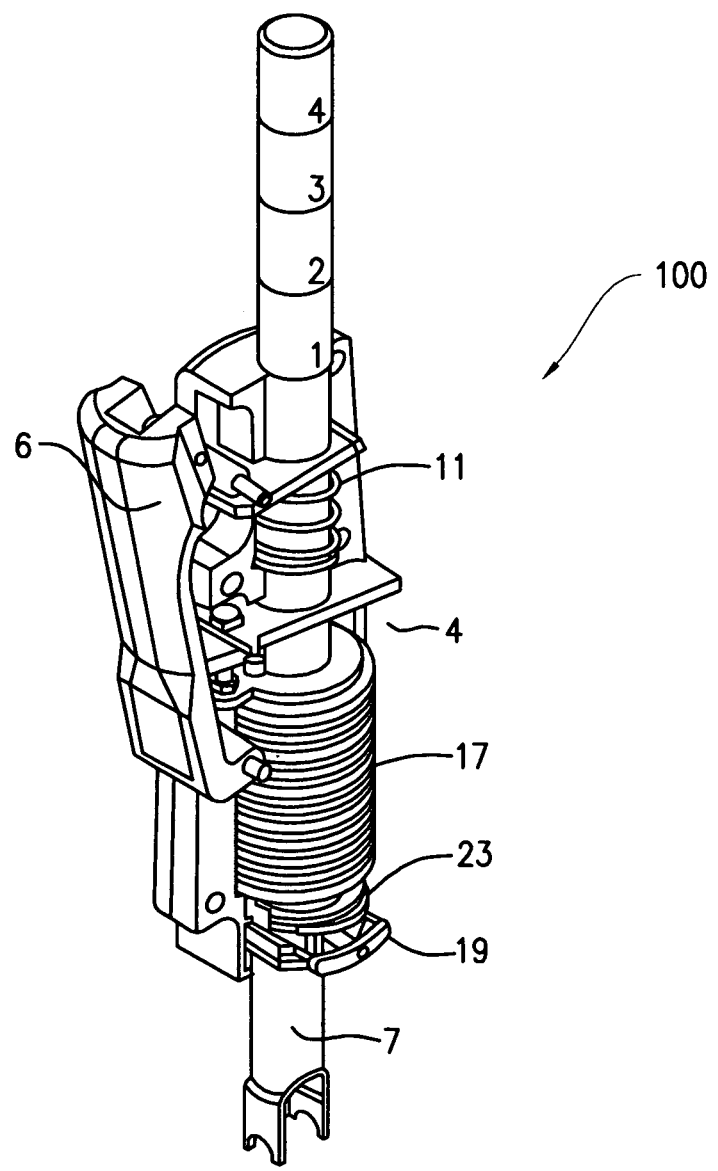
FIG. 1 is a perspective cut-away view of a persuader-reducer device.
Figure 3:
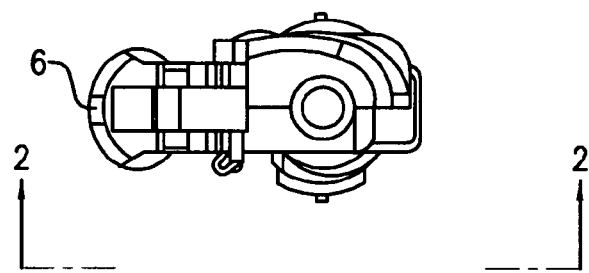
FIG. 3 is a top view of the persuader-reducer device of FIG. 2.
Figure 2:
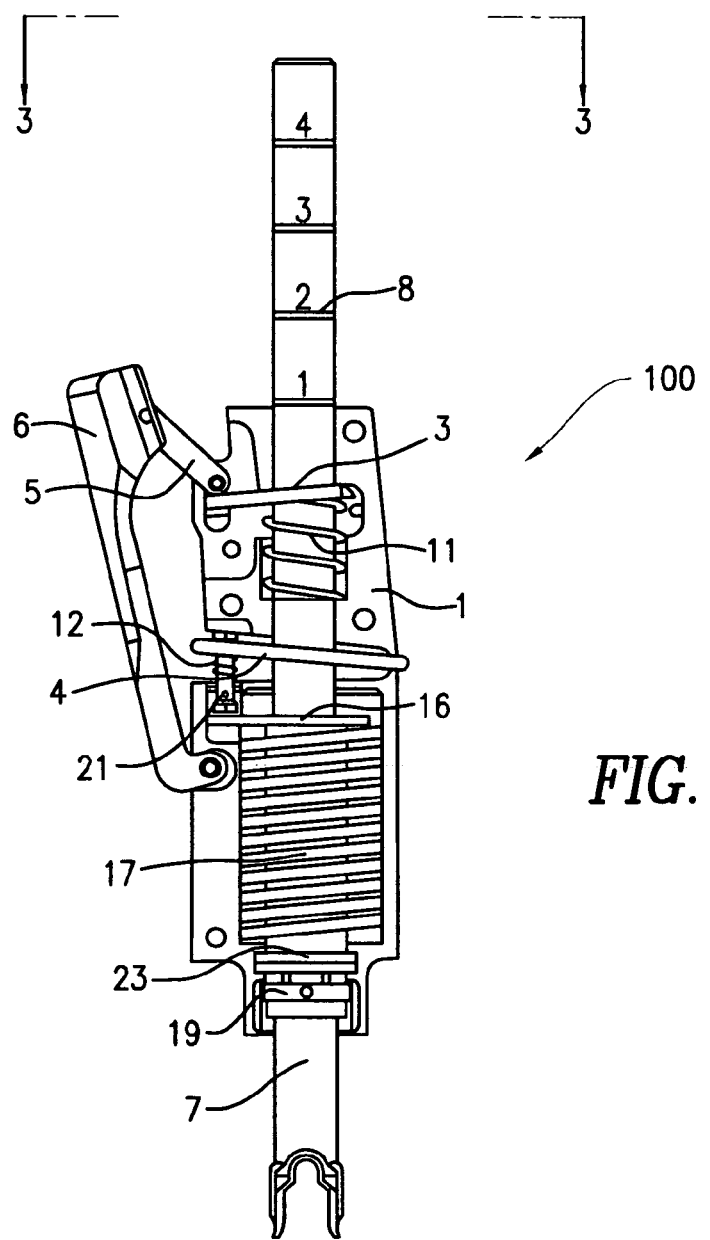
FIG. 2 is a side cutaway view of a persuader-reducer device.
Figure 4:
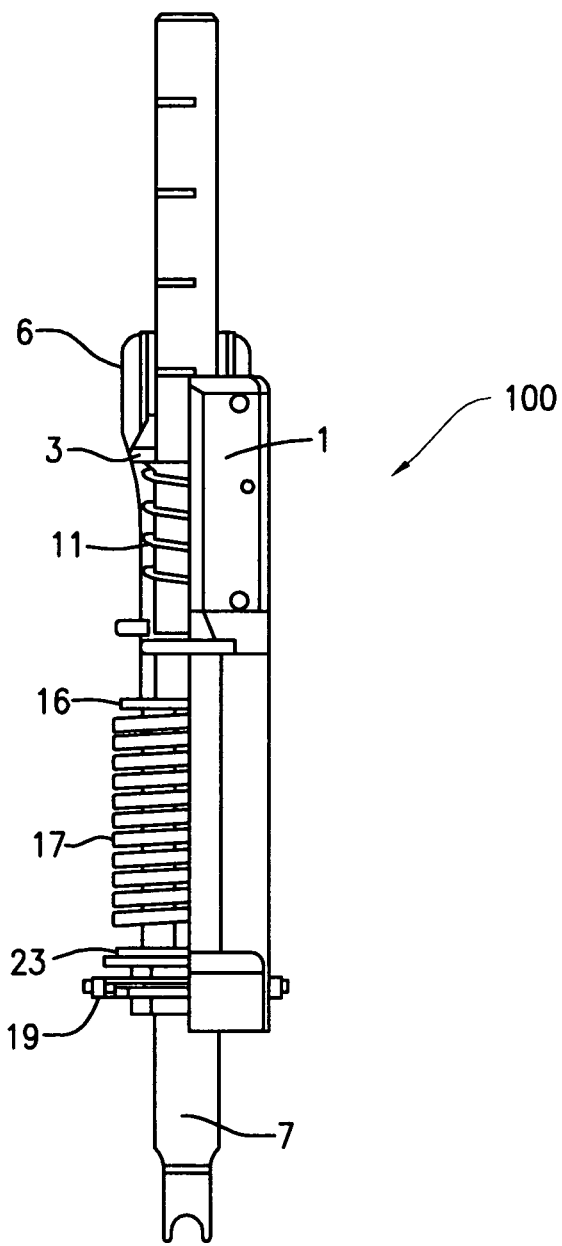
FIG. 4 is a side view, partial cutaway view of a persuader-reducer device.
Figure 5:
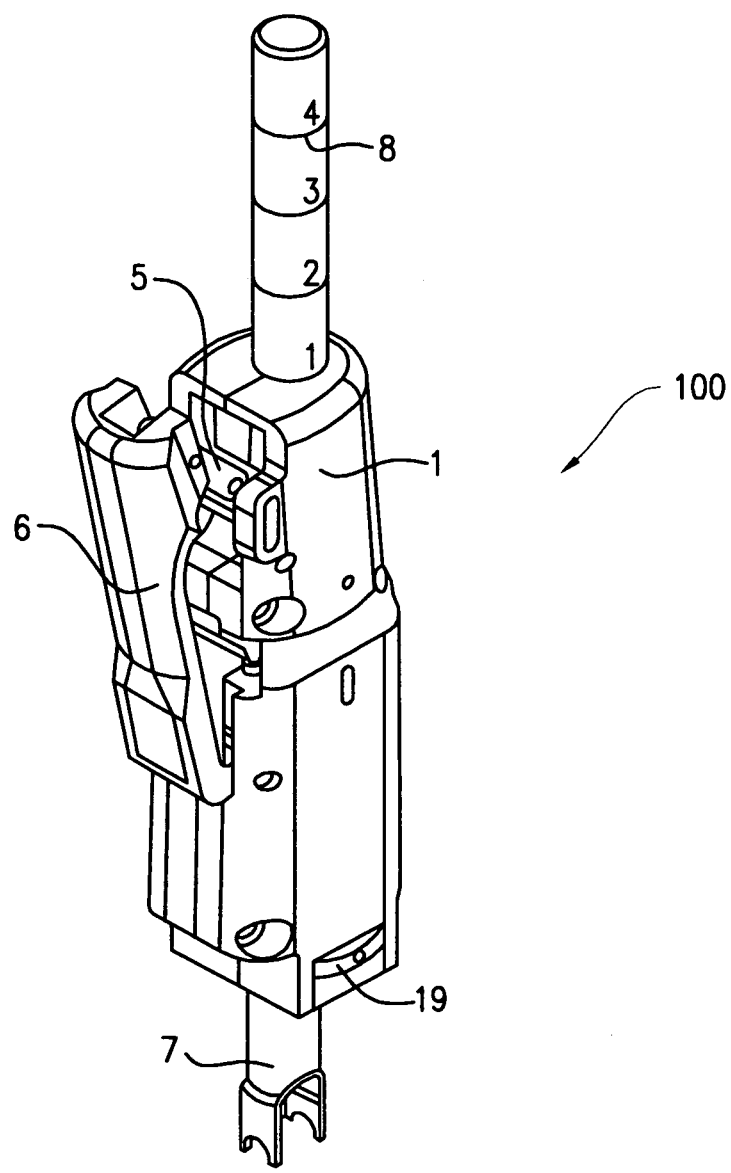
FIG. 5 is a perspective view of a persuader-reducer device.
Figure 7:
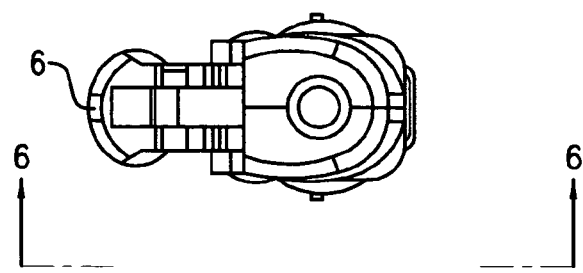
FIG. 7 is a top view of the persuader-reducer device of FIG. 6.
Figure 6:
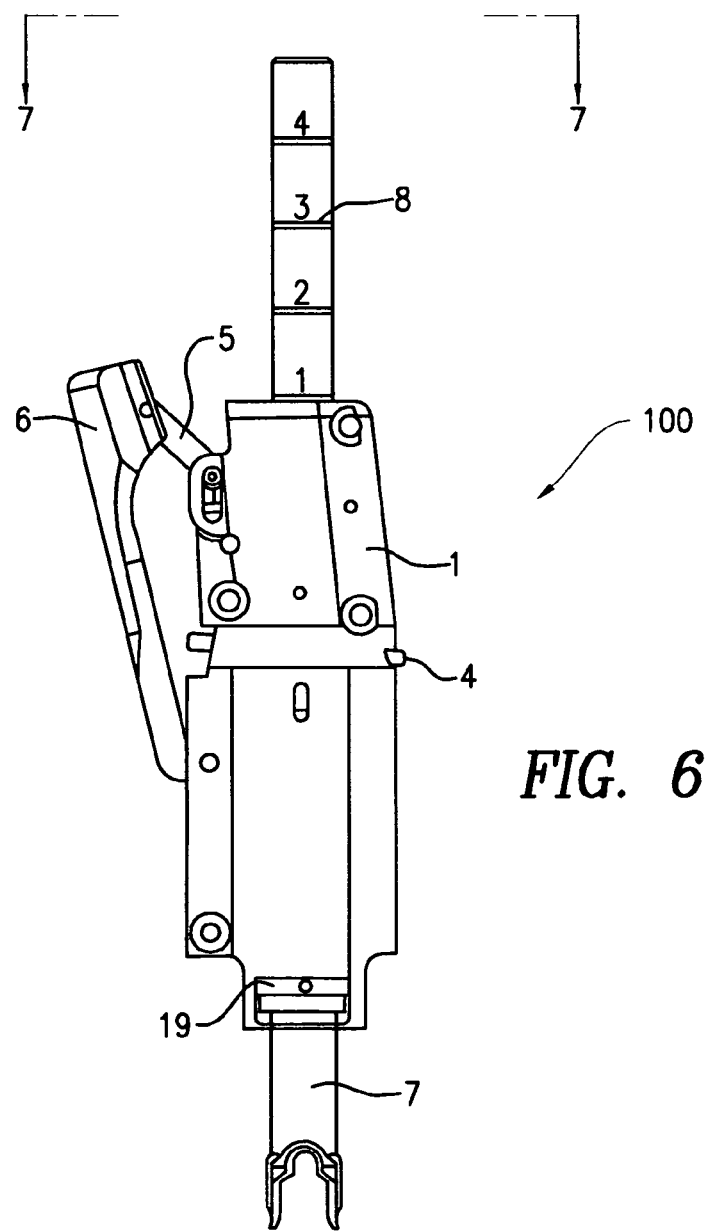
FIG. 6 is a side view of a persuader-reducer device.
Figure 8:
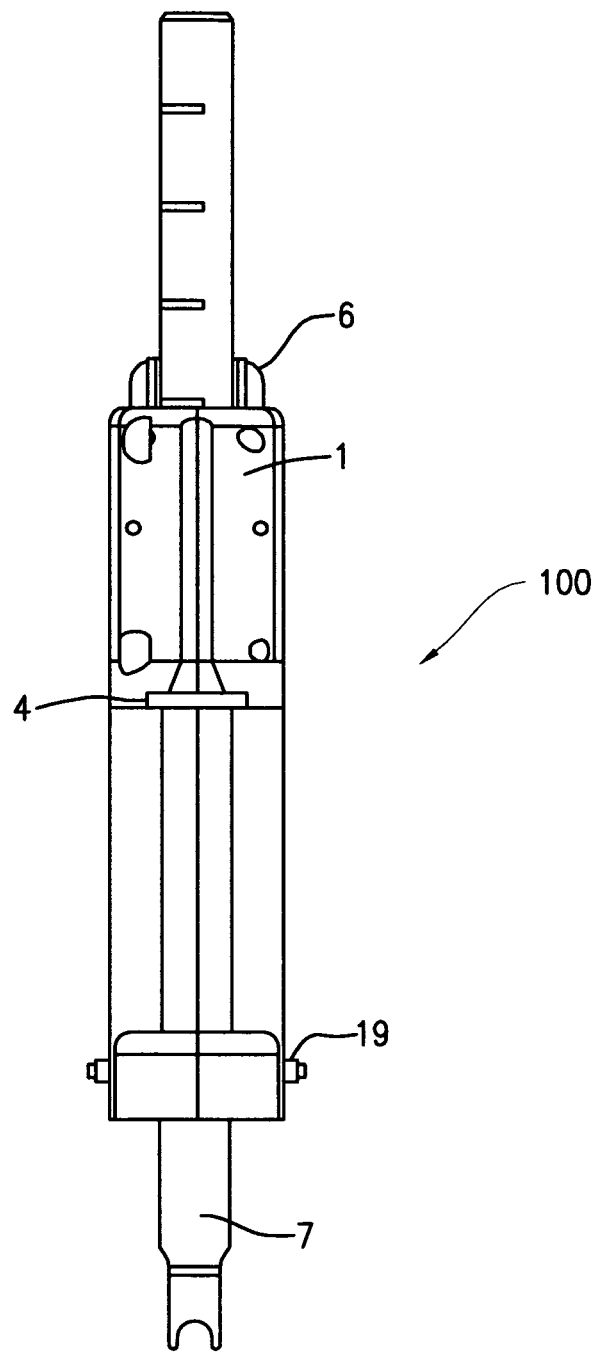
FIG. 8 is a side view of a persuader-reducer device.

FIGS. 1-16 show various aspects of force limiting persuader-reducer devices adapted to apply force to a spinal fixation rod to move it into a fully seated position in a pedicle screw head and allow the subsequent tightening of the pedicle screw fixation means to anchor the spinal fixation rod into place. Due to a number of factors such as anatomical variations, pathologies, rod geometry, and screw head geometry, the rod may require a relatively large force to sufficiently move the rod into the pedicle screw head. The persuader-reducer device may have two modes: the first mode is as a force-limiting persuader where the rod is moved with a relatively lower peak force in the range of ~250-500N into the pedicle screw head, and the second mode is as a full-force reducer where the rod & anatomy are moved with larger loads upwards of ~1200N in an effort to help reduce or correct spondylolisthesis. In the first mode, the device limits the amount of force application and might prevent instrument damage, over-stressing the anatomy, etc. In the second mode, the device permits a much higher force to be applied. That much higher force might be limited only by how much force the user is physically able to apply to the device and the mechanical advantage of the device.

Referring to the FIGS. 1-8, one embodiment of the force limiting persuader-reducer device 100 includes: a handle 1 forming the body of the device, a lever 6, a lever linkage 5, a top rocker plate 3, a top rocker plate biasing member 11, a translating shaft 7, a bottom rocker plate 4, a bottom rocker plate linkage 21, a bottom rocker plate biasing member 12, a movable carriage 16, a main biasing member 17, a blade engagement means 19, and a carriage lockout means 23.

Figure 9:
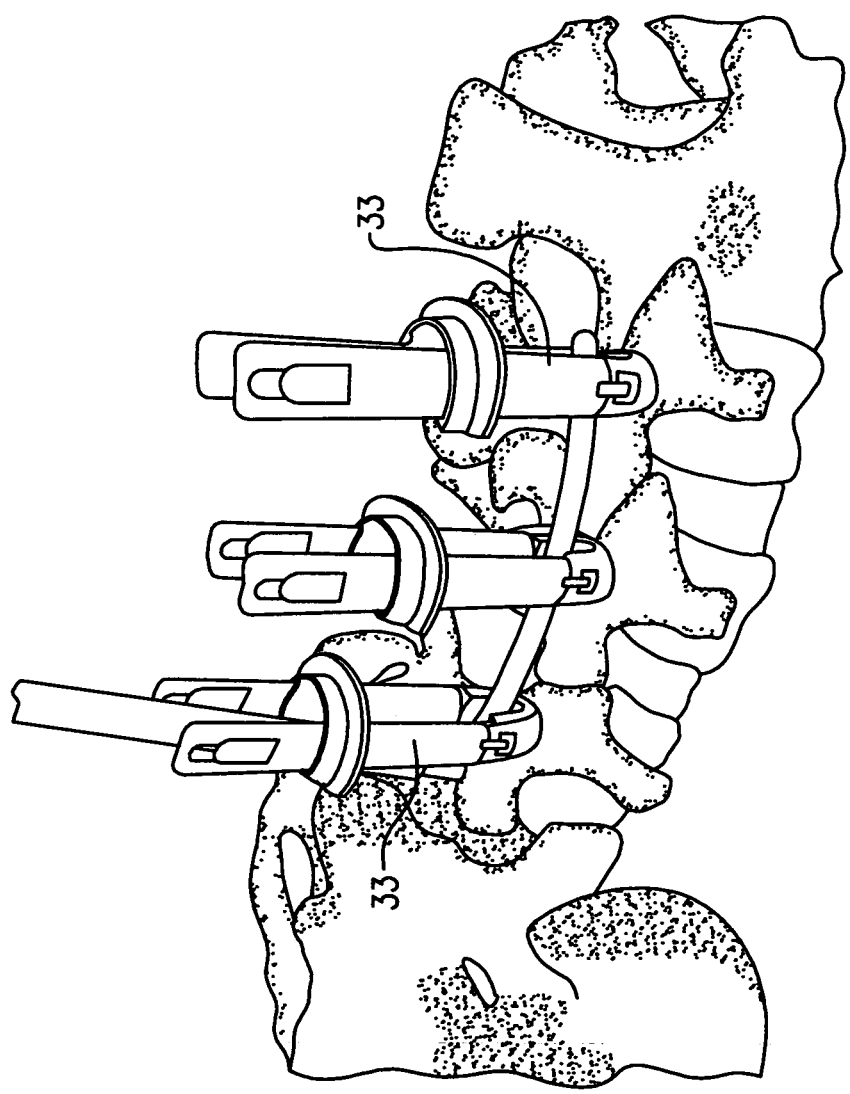
FIG. 9 is a spinal implant rod partially coupled to spinal implant devices.
Figure 10:
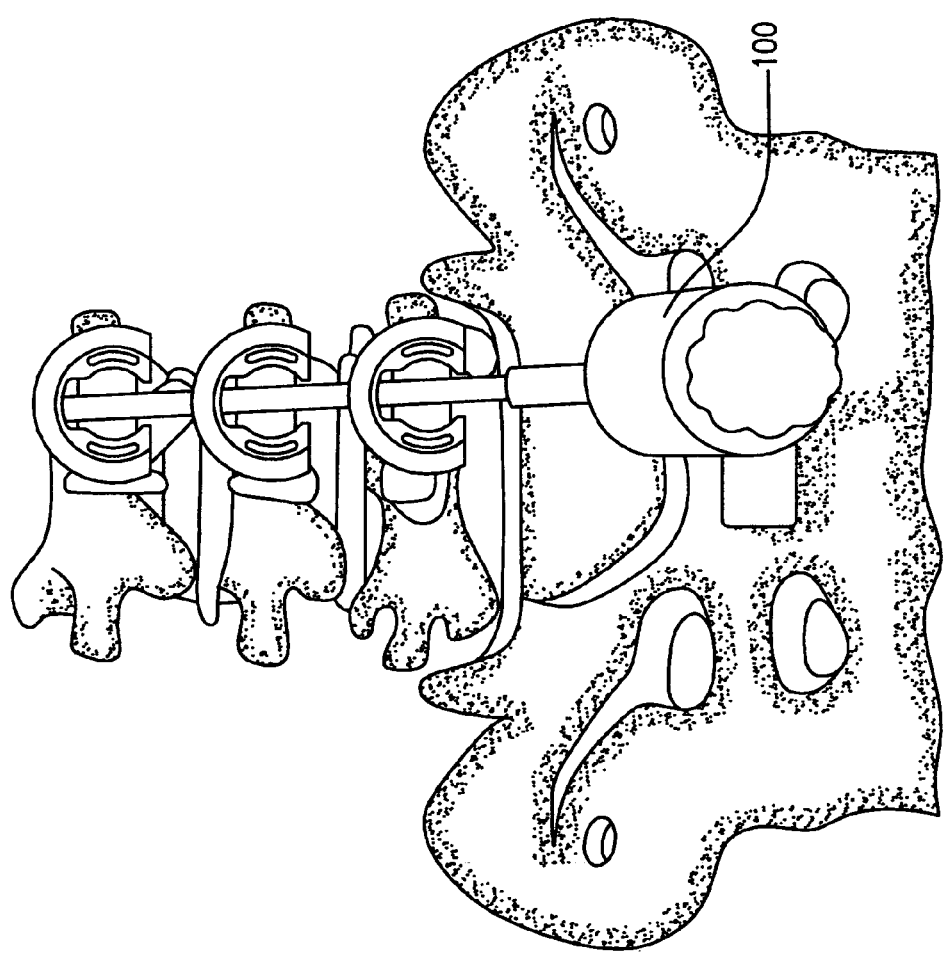
FIG. 10 illustrates a spinal implant rod being coupled to spinal implant devices.
Figure 11:
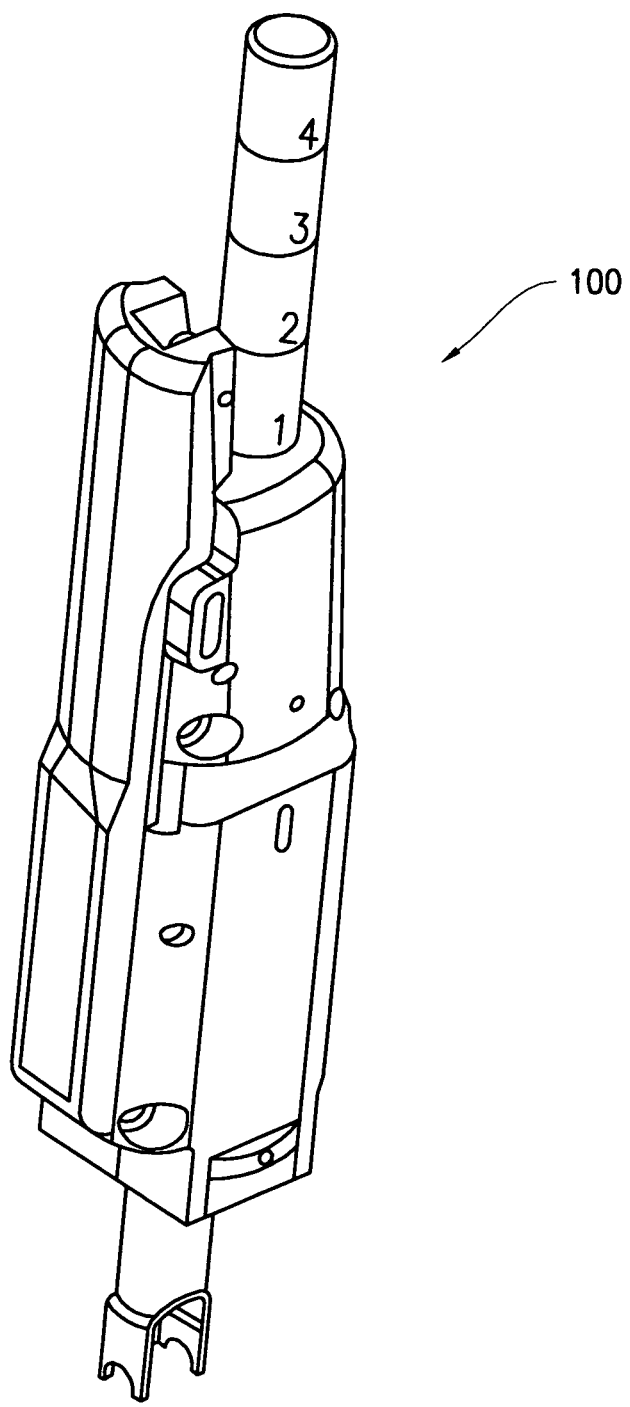
FIG. 11 is a persuader-reducer device.
Figure 12:
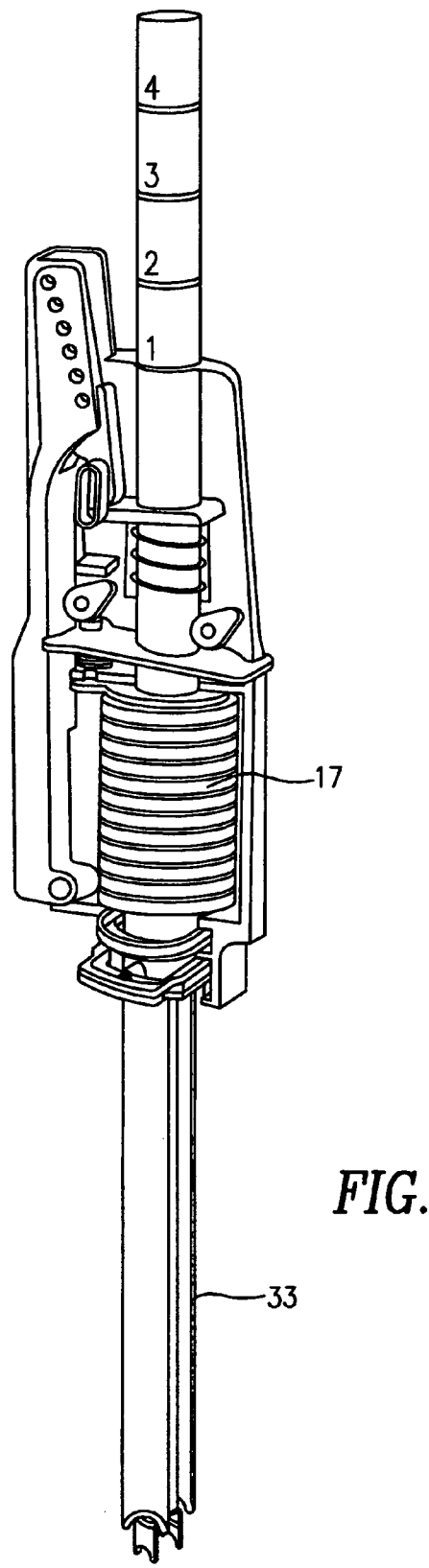
FIG. 12 is a cutaway view of a persuader-reducer device coupled to blades.

In one implementation, the device 100 is adapted to be coupled to one or more retractor blades 33 (FIGS. 9, 10 and 12 of a spinal implant. In particular, the retractor blades 33 can be engaged to the device 100 by being slid into slots of the blade engagement means 19. Exemplary retractor blades 33 are disclosed in commonly assigned patent application entitled "ROD CONTOURING APPARATUS AND METHOD FOR PERCUTANEOUS PEDICLE SCREW EXTENSION," filed Sep. 25, 2006, Ser. No. 11/526,785, which is hereby incorporated by reference in its entirety. The disclosure of patent application entitled "ROD CONTOURING APPARATUS AND METHOD FOR PERCUTANEOUS PEDICLE SCREW EXTENSION," also discloses devices and method for contouring spinal rods into various configurations. The device and methods disclosed herein are particularly well-suited for use with those techniques and devices.

The device 100 is adapted to recognize blade type. Exemplary blades 33 include standard, aluminum blades or reduction, stainless steel blades. The device 100 recognizes blade type by virtue of certain types of blades engaging the device 100 in such a manner that they contact and move a sensor (e.g., a spring biased slide) on the device 100. In one implementation, if a blade contacts and moves a sensor, then the force-limiting function of the device 100 is disabled. When the force-limiting function is enabled, the device 100 is typically adapted to limit loads to <375 N via the spring-biased carriage for aluminum blades.

Figure 16:
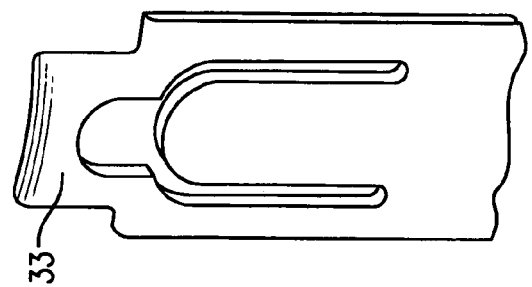
FIG. 16 is a detail view of the end of the reduction blade that is designed for coupling to the persuader-reducer device.
Figure 15:
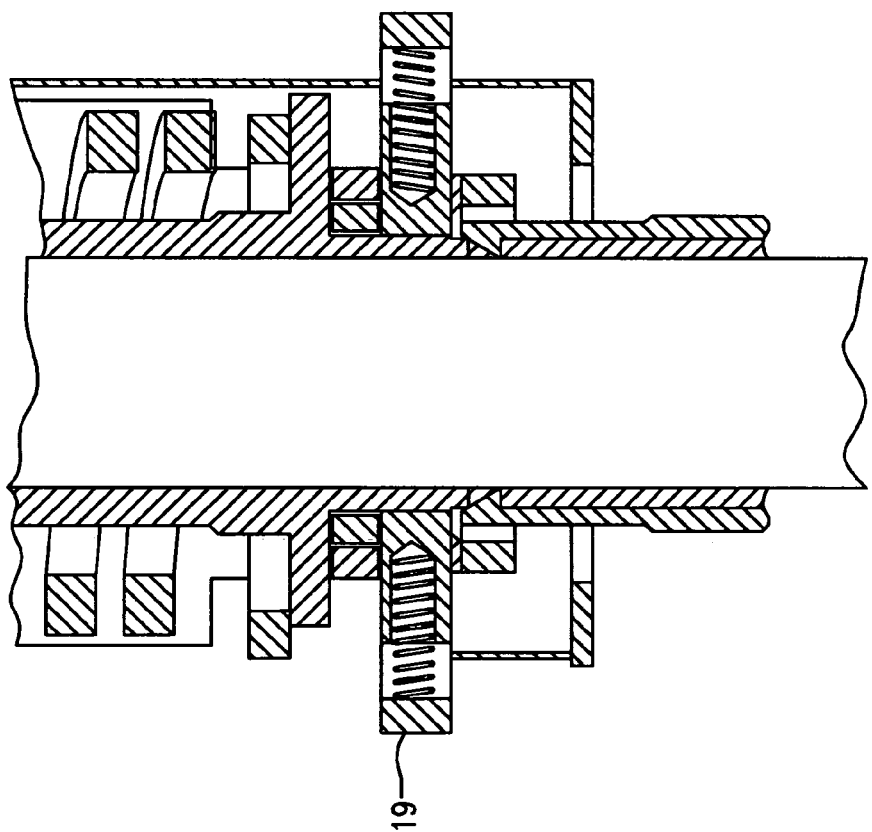
FIG. 15 is a detail view of the retention feature of the persuader-reducer device of FIG. 12.

Referring to the illustrated implementation in FIGS. 1-8, the handle 1 serves to contain and/or support (i.e., provide a body/housing) the working elements of the persuader-reducer device 100 and provides an ergonomic hold of the assembly for the user. The lever 6 is the force input means that the user squeezes to provide an input force. The lever 6 has two pivots: a first pivot about which the lever rotates relative to the handle, and a second pivot about which the lever rotates relative to the lever linkage 5. The lever linkage 5 transmits the force applied to the lever to the top rocker plate 3. The lever linkage 5 also has two pivots: a first pivot about which the lever rotates, and a second pivot about which the top rocker plate 3 rotates. The top rocker plate 3 transmits the force to the translating shaft 7, which moves downward in response to the force to accomplish the persuasion or reduction function. The top rocker plate biasing member 11 serves to provide a counter-moment to the top rocker plate such that the top rocker plate 3 can sufficiently act upon the translating shaft 7. The bottom rocker plate 4 serves to hold the position of the translating shaft 7 once it has displaced and acts similar to a one-way brake by allowing translation in one direction but not the other. (FIG. 13) The force retention bottom rocker plate 4 rotates about a fulcrum contained within the handle 1 and is biased into a holding position by the bottom rocker plate biasing member 12. When the translating shaft 7 advances downward, it slightly rotates the bottom rocker plate 4 and compresses the bottom rocker plate biasing member 12 to allow the translating shaft 7 to translate. Once the downward translation of shaft 7 stops, the bottom rocker plate 4 rotates back to its free state under the force applied via the bottom rocker plate biasing member 12 and prevents the shaft 7 from retracting in an upwards direction. The user can attach the persuader-reducoer device 100 to a spinal implant via retractor blades 33 by engaging the blades 33 with a blade engagement means 19. The preferred embodiment for these blade engagement means 19 are spring-biased pins which engage a hole in the retractor blade (FIGS. 15 and 16). Once the blades 33 are attached, the user can squeeze the lever 6 to apply force and impart displacement to the translating shaft 7.

The translating shaft 7 is adapted at one end to receive the spinal rod and can push it down into the head of the spinal implant (pedicle screw) under the force transmitted by the user through the lever 6. Once the rod is fully seated in the spinal implant, there are indications 8 on the translating shaft 7 which indicate to the user that the spinal rod is fully seated in the spinal implant. The translating shaft 7 has a central bore through which a spinal implant tightening mechanism or device may be inserted and the spinal rod may be tightened down into the spinal implant. Once the spinal rod is tightened, the user can disengage the persuader-reducer device 100 from the retractor blades 33 by pressing on the blade engagement means 19. He can also retract the shaft 7 in the upwards direction by pushing on the bottom rocker plate 4 tabs, which disengages the bottom rocker plate 4 from the translating shaft 7 and allows it to slide freely.

To provide a force-limiting function, there is a bottom rocker plate linkage 21 which will rotate the bottom rocker plate 4 out of holding position once the force gets to a predetermined value. This occurs via a movable carriage 16, a main biasing member 17, and the bottom rocker plate linkage 21. The main biasing member 17 is pre-compressed to a specified force between the handle 1 and the movable carriage 16, which stores potential energy in the main biasing member 17. The movable carriage 16 is connected to the spinal implant retractor blades 33 via the blade engagement means 19 which are in turn connected to the spinal implant. When the force applied via the translating shaft 7 exceeds the potential energy stored in the main biasing member 17 and hits the trigger force, the movable carriage 16 also translates downwards, further compressing the main biasing member 17. Since both the translating shaft 7 and the movable carriage 16 attached to the retractor blades 33 are moving together, there is little relative displacement between the two and the user is prevented from applying excessive force to the construct. The bottom rocker plate linkage 21 is attached to both the bottom rocker plate 4 and the movable carriage 16. When the movable carriage 16 translates downwards in response to the trigger force, the bottom rocker plate linkage 21 also moves downwards and disengages the bottom rocker plate 4, which prevents it from holding the translating shaft 7 in position and in effect prevents it from holding a force that exceeds the pre-compressed force of the main biasing member 17. Once the lever 6 has been squeezed to its full extent, the user must open his grip to reset the instrument. At this instant, the main biasing member 17 pushes the movable carriage 16 upwards to its free state position, which resets the bottom rocker plate linkage 21 and the bottom rocker plate 4 and allows the bottom rocker plate to re-engage with translating shaft 7 and hold it from further upward translation.

To provide the dual function modes as previously indicated (force-limiting persuader and full-force reducer), there is a carriage lockout means 23, which can prevent the movable carriage 16 from moving relative to the handle and thereby eliminate any of its force-limiting function. The carriage lockout means 23, in one embodiment, may be operated manually and slides relative to the moveable carriage 16. The preferred embodiment for this carriage lockout means is a spring-biased slide. In one embodiment, when the persuasion retractor blades 33 are inserted, the spring biased slide does not lock the movable carriage 16 to the handle 1. When the reduction retractor blades 33 are inserted, the spring biased slide locks the movable carriage 16 to the handle 1, removing the force-limiting function and providing a full-force reduction function.

The blade engagement means 19 receives the retractor blades 33. Once the retractor blades 33 are engaged, the user can apply a force (e.g., squeeze) the handle 6 to advance the shaft 7 and push down the rod into the spinal implant.

In certain implementations described above one or more of the following advantages are present. In some implementations, the devices described above act as a combination instrument for rod persuasion and limited spondy reduction. A spinal rod can be percutaneously moved into position into a pedicle screw head when the rod is not seating for some reason and allows subsequent tightening of the set screw onto the spinal rod. Force-limiting persuasion ability may be used to prevent damage to anatomy and/or instruments. The device 100 is adapted to automatically enable force limiting when appropriate and to automatically disable force limiting when inappropriate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention. For example, alternative embodiments for the force input mechanisms exist other than the lever described in the preferred embodiment, such as: levers with compound linkages, triggers, twisting mechanisms, etc. Alternative embodiments for the rocker plates also exist to transmit the force input to the translating shaft, such as: pinion gears, worm gears, threads, rack & pinions, etc. Alternative embodiments for the force-limiting means also exist, such as: discrete steps in the translating shaft which will engage a spring-biased plate when the shaft is in the fully seated position, and various spring biased gear mechanisms which only permit the gear to engage with the translating shaft when the force is lower than the trigger force. Other methods for enabling or disabling the force-limiting feature are possible.

Additionally, the device 100 disclosed herein could be adapted to include only a force limiting mode of operation. In that instance, regardless of blade type, the force-limiting feature would be enabled.

The invention claimed is:

1. An apparatus for advancement of a spinal rod in a spinal implant, the apparatus comprising:
    a body;
    a lever attached to the body;
    a shaft slidably attached to the body, such that the shaft is slidable relative to the body along a longitudinal axis of the shaft, the shaft being coupled to the lever and having a first end adapted to engage the spinal rod; and
    at least one retractor blade, the retractor blade having a first end adapted to attach to the body and a second end adapted to be attached to the spinal implant,
    wherein compressing the lever towards the body causes the first end of the shaft to move away from the body along the longitudinal axis to persuade the spinal rod into the spinal implant, and wherein the force exerted by the shaft on the spinal rod is limited to a pre-selected force.

2. The apparatus of claim 1, further comprising:
    a biasing member attached to the body; and
    a movable carriage attached to the biasing member,
    wherein the biasing member exerts the pre-selected force on the movable carriage.

3. The apparatus of claim 2, wherein the pre-selected force is less than 375 N.

4. The apparatus of claim 2, further comprising:
a pivotable rocker plate, the pivotable rocker plate adapted to lock the shaft such that the shaft is stopped from retracting from engagement with the spinal rod.

5. The apparatus of claim 4, further comprising:
indications formed on the shaft, the indications capable of indicating to the user that the spinal rod is fully seated in the spinal implant.

6. The apparatus of claim 4, further comprising:
a carriage lock, the carriage lock capable of locking the movable carriage to disable the pre-selected force and to allow all the force applied to the lever to be transmitted to the spinal rod via the shaft.

7. A persuasion and reduction apparatus for advancement of spinal rod in a spinal implant, the apparatus comprising:
a body;
a shaft slidably attached to the body, the shaft having a first end adapted to engage the spinal rod;
a force input mechanism operably coupled to the shaft, wherein operation of the force input mechanism results in the shaft persuading the spinal rod into the spinal implant;
a force limiting mechanism; and
at least one first retractor blade, the first retractor blade having a first end adapted to attach to the body and a second end adapted to be attached to the spinal implant,
wherein the force limiting mechanism has an activated mode and a de-activated mode, a force exerted by the first end of the shaft on the spinal rod being limited to a pre-selected force when the force limiting mechanism is in the activated mode, and all of an applied force being transferred from the force input mechanism to the spinal rod via the shaft when the force limiting mechanism is in the de-activated mode.

8. The apparatus of claim 7, further comprising:
a biasing member attached to the body; and
a movable carriage attached to the biasing member,
wherein the biasing member exerts the pre-selected force on the movable carriage.

9. The apparatus of claim 8, wherein the pre-selected force is less than 375 N.

10. The apparatus of claim 8, further comprising:
a pivotable rocker plate, the pivotable rocker plate adapted to lock the shaft such that the shaft is stopped from retracting from engagement with the spinal rod.

11. The apparatus of claim 10, further comprising:
indications formed on the shaft, the indications capable of indicating to the user that the spinal rod is fully seated in the spinal implant.

12. The apparatus of claim 10, further comprising:
a carriage lock, the carriage lock locking the movable carriage when the force limiting mechanism is in the de-activated mode.

13. The apparatus of claim 7, wherein attaching the first end of the first retractor blade to the body enables the activated mode of the force limiting mechanism.

14. The apparatus of claim 13, further comprising at least one second retractor blade having a first end adapted to attach to the body and a second end adapted to be attached to the spinal implant, wherein attaching the first end of the second retractor blade to the body enables the de-activated mode of the force limiting mechanism.

15. The apparatus of claim 7, wherein the force input mechanism is a lever.

16. A method of advancing a spinal rod in a spinal implant, the method comprising the steps of:
implanting a first spinal implant in a first vertebra;
implanting a second spinal implant in a second vertebra;
placing a rod in the first and the second implant;
attaching at least one persuasion retractor blade to the first vertebra;
attaching a persuading and reducing apparatus to the persuasion retractor blade, the apparatus having a force limiting mode, such that the apparatus applies a force on the rod that is less than a pre-selected force;
operating a handle on the persuading and reducing apparatus while the device is in the force limiting mode to advance a shaft and thereby persuade the rod in the first spinal implant, the shaft applying a force on the rod that is less than the pre-selected force; and
de-activating the force limiting mode, whereby all of a force exerted on the shaft is transmitted to the spinal rod.

17. The method of claim 16, further comprising the steps of:
attaching at least one reduction retractor blade to the second vertebra;
attaching the persuading and reducing apparatus to the reduction retractor blade; and
operating the handle on the persuading and reducing apparatus to advance a shaft and thereby advance the rod in the second spinal implant thereby reducing the second vertebra.

18. The method of claim 17, further comprising the steps of:
locking the shaft in the advanced position to hold the rod in the implant; and
inserting a screw in the first and the second spinal implant to hold the rod in place.

19. The method of claim 17, wherein the reduction retractor blade has a first end adapted to be coupled to the persuading and reducing apparatus, and wherein coupling of the first end of the reduction retractor blade to the persuading and reducing apparatus automatically de-activates the force limiting mode of the persuading and reducing apparatus.

20. An apparatus for advancement of a spinal rod in a spinal implant, the apparatus comprising:
a body having a force input mechanism and a shaft slidably attached to the body, wherein the operation of the force input mechanism results in the shaft persuading the spinal rod in the spinal implant, the body being adapted to detachably receive a first retractor blade, such that receiving the first retractor blade by the body activates a force limiting mechanism such that a force exerted by the shaft on the spinal rod cannot exceed a pre-selected force.

21. The apparatus of claim 20, wherein the body is adapted to receive a second retractor blade in place of the first retractor blade, the second retractor blade operating to de-activate the force limiting mechanism such that all of a force exerted on the shaft is transmitted to the spinal rod.

22. The apparatus of claim 21, wherein the first retractor blade is made from aluminum and the second retractor blade is made from steel.

23. An apparatus for advancement of a spinal rod in a spinal implant, the apparatus comprising:
a body;
a biasing member attached to the body;
a movable carriage attached to the biasing member;
a force input mechanism attached to the body;

a shaft slidably attached to the body, the shaft being coupled to the force input mechanism and having a first end adapted to engage the spinal rod;

at least one retractor blade, the retractor blade having a first end adapted to attach to the body and a second end adapted to be attached to the spinal implant; and a carriage lock, wherein the operation of the force input mechanism results in the shaft persuading the spinal rod in the spinal implant, wherein the force exerted by the shaft on the spinal rod is limited to a pre-selected force, wherein the biasing member exerts the pre-selected force on the movable carriage, and wherein the carriage lock is capable of locking the movable carriage to disable the pre-selected force and to allow all the force applied to the force input mechanism to be transmitted to the spinal rod via the shaft.

24. The apparatus of claim 23, wherein the pre-selected force is less than 375 N.

25. The apparatus of claim 23, further comprising:
a pivotable rocker plate, the pivotable rocker plate adapted to lock the shaft such that the shaft is stopped from retracting from engagement with the spinal rod.

26. The apparatus of claim 25, further comprising:
indications formed on the shaft, the indications capable of indicating to the user that the spinal rod is fully seated in the spinal implant.

27. A method of advancing a spinal rod in a spinal implant, the method comprising the steps of:
implanting a first spinal implant in a first vertebra;
implanting a second spinal implant in a second vertebra;
placing a rod in the first and the second implant;
attaching at least one retractor blade to the first vertebra;
attaching a persuading and reducing apparatus to the retractor blade, the apparatus having a force limiting mode, such that the apparatus applies a force on the rod that is less than a pre-selected force;
operating a force input mechanism on the persuading and reducing apparatus while the device is in the force limiting mode to advance a shaft and thereby persuade the rod in the first spinal implant, the shaft applying a force on the rod that is less than the pre-selected force; and
de-activating the force limiting mode, whereby all of a force exerted on the shaft is transmitted to the spinal rod.

* * * * *